United States Patent [19]

McCoy

[11] Patent Number: 5,360,392
[45] Date of Patent: Nov. 1, 1994

[54] METHOD OF FORMING A SCOLIOSIS BRACE

[75] Inventor: D. Barry McCoy, Exeter, R.I.

[73] Assignee: Northeast Orthotics & Prosthetics, Inc., Providence, R.I.

[21] Appl. No.: 61,672

[22] Filed: May 14, 1993

[51] Int. Cl.$^5$ .................. A61F 5/02; A61G 13/00
[52] U.S. Cl. .................................. 602/6; 602/8; 602/19; 602/33; 602/36; 602/54; 5/621; 5/632
[58] Field of Search ............... 606/237, 238, 240, 241, 606/54, 60, 61; 602/6, 8, 19, 32, 33, 36; 128/845; 5/621, 632

[56] References Cited

U.S. PATENT DOCUMENTS 4,202,327  5/1980  Glancy .................................. 602/19
5,096,173  3/1992  Yamashita et al. ..................... 5/621

*Primary Examiner*—Stephen R. Crow
*Assistant Examiner*—Beverly A. Meindl
*Attorney, Agent, or Firm*—Salter & Michaelson

[57] ABSTRACT

An apparatus for forming a brace for a scoliosis patient includes a casting board for receiving a patient in a laying-down position and a plurality of pressure pads which are releaseably securable on the casting board for applying lateral pressure to the torso portion of the patient. The apparatus is operative in a method for forming a brace by first positioning the patient in a treatment position on the casting board in which the pressure pads are assembled with the patient to apply predetermined amounts of lateral pressure to precisely defined areas of the torso portion of the patient. The patient is then removed from the casting board, an uncured cast is assembled on the torso portion of the patient and the patient is repositioned in the same treatment position on the casting board while the cast is allowed to cure. The cast can then be used to form a scoliosis brace for the patient by conventional techniques.

16 Claims, 4 Drawing Sheets

METHOD OF FORMING A SCOLIOSIS BRACE

BACKGROUND AND SUMMARY OF THE INVENTION

The instant invention relates to the treatment of scoliosis and more particularly to a method of forming a corrective brace for a scoliosis patient and to an apparatus utilized in the method.

Lateral curvature of the spine, commonly known as scoliosis, has been found to be a potentially disabling progressive physical condition which affects a significant segment of the adolescent and adult population. However, it has been further found that in many instances, scoliosis can be corrected or cured if treated at an early stage in its progression. In this regard, it is generally accepted that there are two basic methods of treating scoliosis depending on the degree of severity. Specifically, in cases where scoliosis is caught at a relatively early stage, it is frequently possible to correct the condition by applying corrective lateral pressure to the appropriate areas of the spinal column of a patient utilizing a scoliosis brace. However, in most instances, the heretofore available scoliosis braces have been less than entirely effective for applying the correct amounts of lateral pressure to precisely the correct areas of the spinal column. Nevertheless, the main heretofore known alternative has been to perform spinal surgery in which the most severely curved areas of the spine are fused to a steel rod and hence, permanently immobilized.

The instant invention provides an effective new method of forming a scoliosis brace which has a substantially increased level of effectiveness for applying the correct amounts of lateral pressure to precisely the correct areas of the spinal column in order to correct lateral curvature thereof. More specifically, the instant invention provides an effective method of positioning a patient prior to and during the fabrication of a cast used in the formation of a scoliosis brace, whereby the brace can be more effectively and accurately tailored to meet the precise needs of the patient. Still more specifically, the method of the instant invention for forming a scoliosis brace comprises the steps of preparing an X-ray of the spine of the patient and positioning the X-ray in substantially aligned relation to the patient to determine the locations of the apex and ends of one or more lateral curves in the patient's spine relative to the exterior of the patient's torso. In this latter step markings are preferably applied to the exterior of the torso portion of the patient to indicate the precise locations of the apex and ends of each lateral spinal curve including each compensatory or reverse curve. The method thereafter further comprises the step of positioning the patient in a face-up, laying-down position on a casting board and applying appropriate amounts of pressure to opposite sides of the torso portion of the patient utilizing at least three pressure pads. The pressure pads are positioned on the casting board in pressure applying positions in which they are operative for applying desired amounts of pressure to the spine at substantially the ends and apex of each lateral curve therein. In this regard, in cases with patients having compensatory or reverse spinal curves, it is generally necessary to utilize a total of at least four pressure pads so that pressure can also be applied to the apex and ends of each curve. In this regard, however, as is well known in the art, in many instances it is necessary to apply pressure to the spine by applying pressure to the sides of the torso portion of a patient at locations which are not directly laterally aligned with the ends or apex of a lateral curve in order to compensate for the various angular dispositions of the ribs of the patient through which pressure is transmitted to the spine. However, the techniques for determining the appropriate locations for applying lateral pressure to the sides of the torso portion of a patient relative to the designated areas of the spinal column are well known in the medical art. In any event, the pressure pad(s) on one side of the torso portion are preferably adjustable for applying variable amounts of pressure to the apex of the scoliotic curve, and the adjustable pad preferably includes a pressure sensor for detecting the precise amounts of pressure applied to the patient therewith. Further, once the pressure pads have been adjusted to apply the desired amounts of pressure to the appropriate areas of the spinal column, the locations of the pressure pads on the casting board which represent the desired pressure applying positions and the treatment position of the patient on the casting board are noted, and one or more of the pressure pads and the patient are removed from the casting board. Thereafter, the method comprises applying an uncured cast to the torso portion of the patient and repositioning the patient on the casting board. Specifically, the patient is repositioned in the same treatment position, and the pressure pads are repositioned in the same pressure applying positions on the casting board. Thereafter, the cast is allowed to cure while the patient is retained in the treatment position with the pressure pads which are retained in the pressure applying positions thereof. Finally, after the cast has cured, the patient with the cast thereon is removed from the casting board along with the pressure pads. The cast is then removed from the patient and the cast is utilized as a mold for forming a scoliosis brace by otherwise conventional techniques. Specifically, the cast is preferably utilized for forming a positive impression of the torso portion of the patient, and the positive impression is then utilized for forming a brace for the patient by conventional techniques.

The apparatus of the instant invention which is operable in the method comprises a casting board for receiving a patient in a face-up laying-down position thereon and at least three pressure pads for applying pressure to opposite sides of the torso portion of the patient. The pressure pads are repeatably releasably securable to the casting board in a plurality of predetermined positions thereon. The casting board preferably has a matrix of predetermined positions thereon, which is defined by a plurality of adjacent rows of pressure pad receiving positions for repeatably receiving the pressure pads thereon. In one embodiment the pressure pad receiving positions are defined by apertures in the casting board, and in this embodiment the apparatus includes pins which are releasably receivable in the apertures in the casting board for releasably securing the pressure pads in position. Further, at least one of the pressure pads preferably includes means for adjustably applying pressure to the torso portion of a patient, and at least one of the pressure pads preferably includes means for determining the amount of pressure applied to the torso portion of a patient therewith.

It has been found that the method and apparatus of the instant invention can be effectively utilized for forming a brace which is operative for applying corrective amounts of pressure to prespecified localized areas of the spinal column of a patient. In this regard, it has been found that by positioning a plurality of pressure pads in the appropriate corrective locations relative to a patient before forming a cast on the patient and by then repositioning the patient and the pressure pads in the same relative positions after an uncured cast has been applied to the patient, it is possible to form the cast in a configuration which enables it to be utilized for forming a highly effective corrective brace for the patient. Specifically, it has been found that it is possible to form a corrective brace which is capable of precisely applying controlled pressures to predetermined localized areas of the spinal column of the patient.

Accordingly, it is a primary object of the instant invention to provide an improved method of forming a brace for a scoliosis patient.

Another object of the instant invention is to provide a method of forming a brace which is capable of effectively and accurately applying predetermined amounts of lateral pressure to predetermined areas of the spinal column of a patient.

Another object of the instant invention is to provide an effective apparatus for positioning a scoliosis patient during the formation of cast for forming a corrective brace for the patient.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
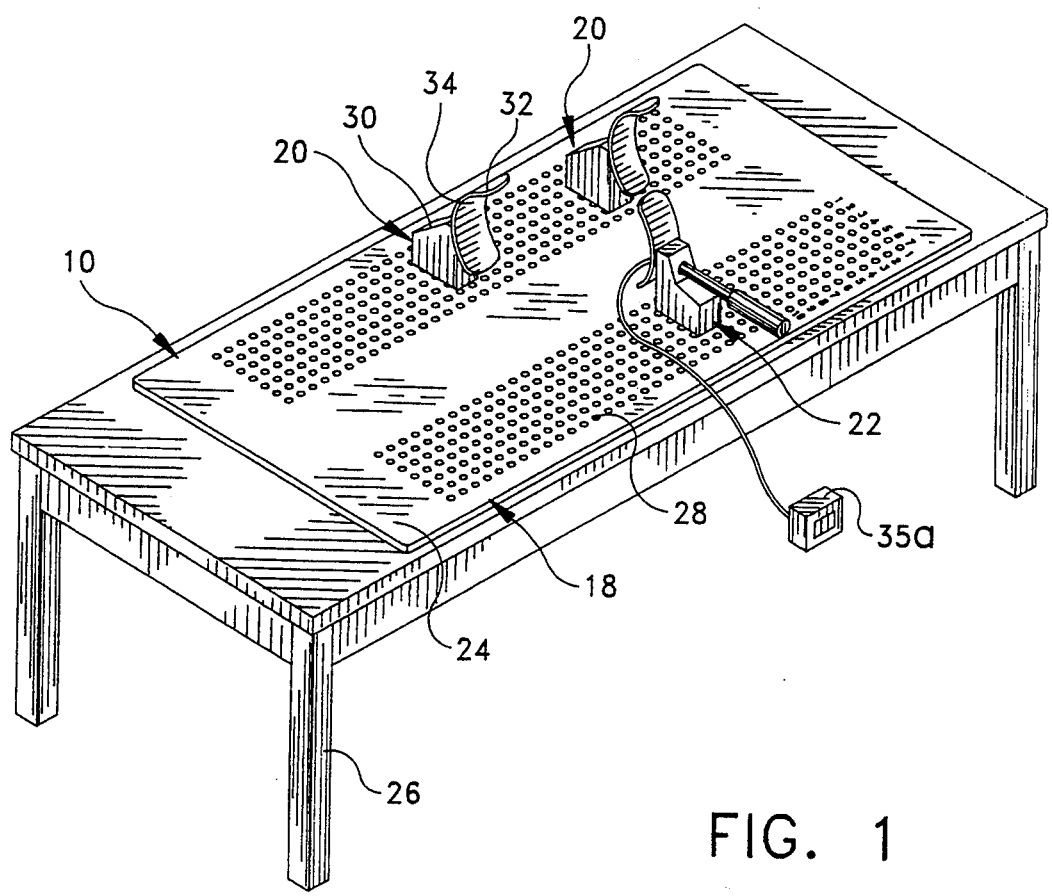
FIG. 1 is a perspective view of the apparatus of the instant invention as positioned on a patient table.

Referring now to the drawings, the apparatus of the instant invention is illustrated and generally indicated at 10 in FIGS. 1 through 5. The apparatus 10 is operative in accordance with the method of the subject invention for positioning a patient generally indicated at 12 during the formation of a cast 14 for use in forming a scoliosis brace generally indicated at 16 for the patient 12. The apparatus 10 comprises a casting board generally indicated at 18, a plurality of stationary pads 20 and an adjustable pad generally indicated at 22. The apparatus 10 is operative in the manner illustrated in FIGS. 3 through 5 for properly positioning the patient 12 during the fabrication of a cast 14 used in forming the brace 16 so as to enable the brace 16 to be effectively utilized for applying controlled amounts of lateral pressure to precisely the correct areas of the spinal column of the patient 12, as will hereinafter be more fully set forth.

Figure 3:
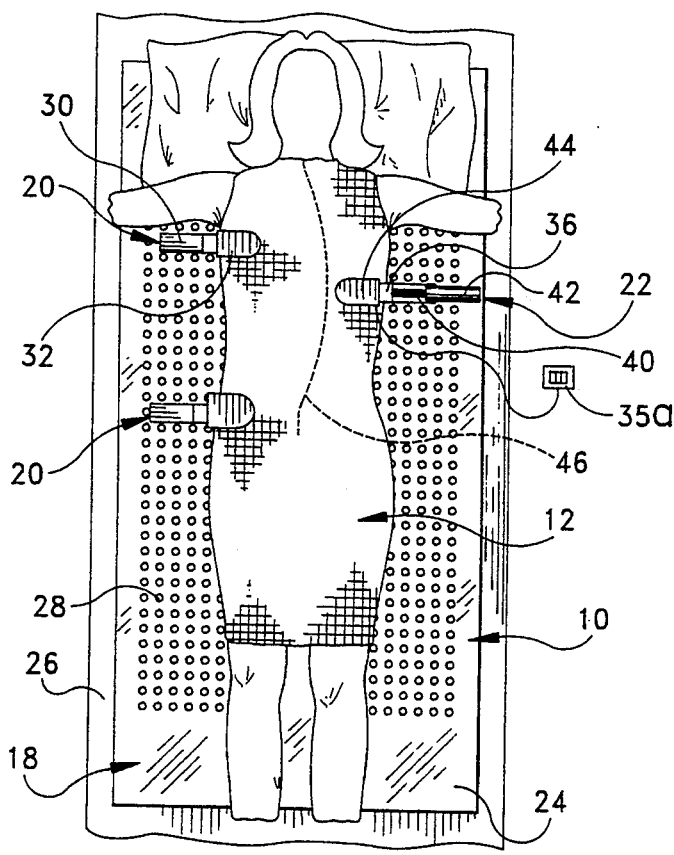
FIG. 3 is a top plan view of the apparatus as utilized for applying pressure to the spine of a patient.
Figure 4:
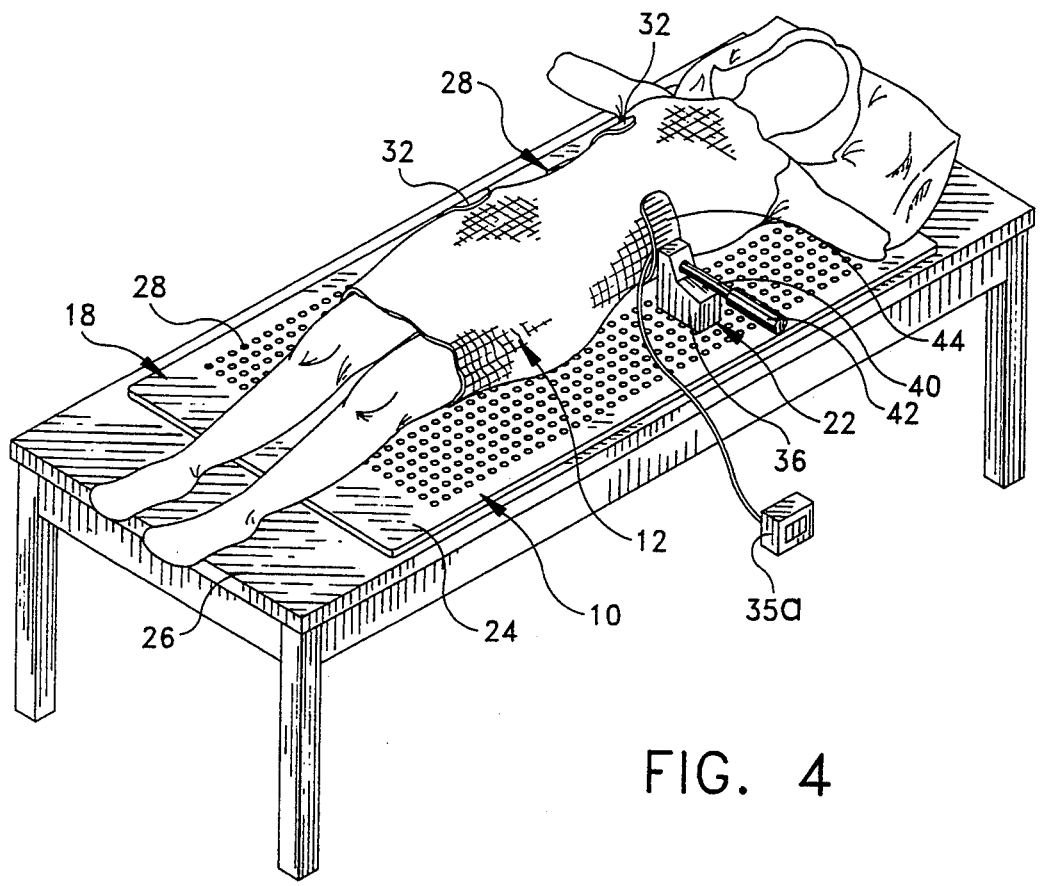
FIG. 4 is a perspective view thereof.
Figure 5:
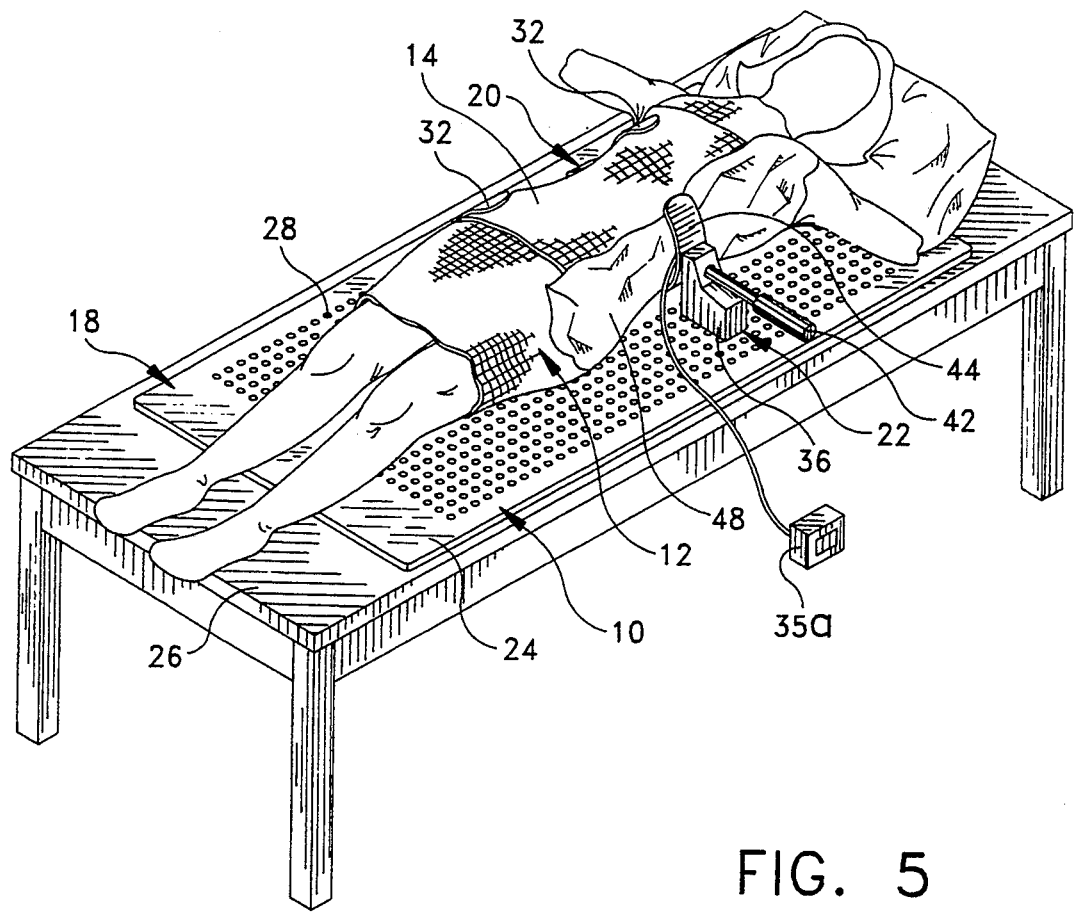
FIG. 5 is a perspective view thereof with a cast received on the patient.
Figure 6:
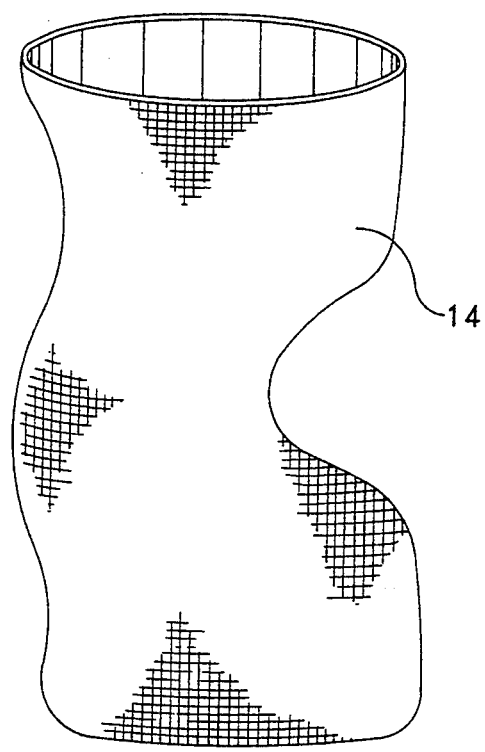
FIG. 6 is a perspective view of the cast subsequent to curing thereof.

The casting board 18 preferably comprises a substantially flat rigid elongated board member 24 which is dimensioned for receiving the patient 12 thereon in the manner illustrated in FIGS. 3 through 5. The board member 24 is preferably supported in upwardly spaced relation to a supporting floor surface on a table 26 to enable the apparatus 10 to be more easily and effectively manipulated by a casting technician. The casting board 24 preferably has a matrix of substantial aligned rows of uniformly spaced apertures 28 therein which are preferably numerically referenced for readily designating various specific locations for positioning the pressure pads 20 and 22 on the casting board 24. In this regard, however, it will be understood that while the casting board 24 as herein embodied includes the apertures 28 for positioning the pressure pads 20 and 22 in various designated locations on the upwardly facing surface thereof, this basic function can alternatively be performed by various other known means. However, the casting board 18 as herein embodied has been found to be effective for repeatably releasably receiving and positioning the pressure pads 20 and 22 at specific and easily referenced locations on the upper surface thereof.

The pressure pads 20 each comprise a body or block portion 30 and a plurality pins (not shown) which are received in apertures on the underside of the block portion 20 and adapted to be snugly, yet easily, releasably, received in the apertures 28 in the casting board 18. Each of the pads 20 further comprises an arcuate pad portion 32 which is adapted and configured for comfortably engaging a side of the torso portion of a patient 12 in order to apply lateral pressure to the torso portion which is transmitted to the spinal column of the patient 12 through the adjacent ribs. Each of pad portions 32 preferably has a slightly padded inner surface 34 for enabling each of the pad portions 32 to be more comfortably and effectively utilized for applying pressure to the patient 12.

Figure 2:
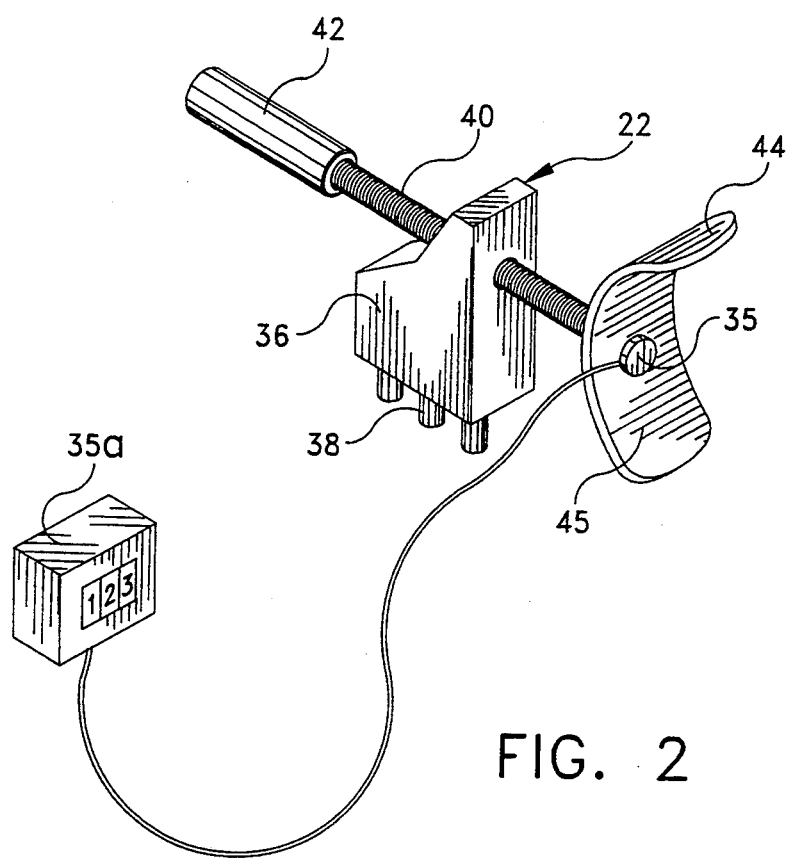
FIG. 2 is a perspective view of an adjustable pressure pad thereof.

The pressure pad 22 is illustrated most clearly in FIG. 2, and it includes a block or body portion 36 and a plurality of downwardly extending pins 38 which are received in apertures on the underside of the block portion 20 and preferably adapted to be snugly yet easily releasably received in the apertures 28 in the board 24. The pressure pad 22 further comprises a threaded shaft 40 having a terminal handle 42 thereon and a pressure pad element 44. The threaded shaft 40 is received in threaded engagement in the body portion 36, and the pressure pad element 44 is rotatably secured to an end of the threaded rod 40 as illustrated. Accordingly, the pressure pad 22 is operable for adjustably positioning the pad element 44 relative to the body portion 36 to enable the pressure pad 22 to be utilized for adjustably applying lateral pressure to the torso portion of the patient 12. The pad element 44 preferably also includes an inwardly facing concave surface 45, which is preferably slightly padded to provide increased patient comfort, and a load cell 35 having a digital read out 35a on the concave surface 45.

For use of the apparatus 10 in accordance with the method of the subject invention, an X-ray is taken of the torso portion of the spine 46 of the patient 12. The X-ray is preferably taken from in front of the patient 12 with the patient 12 facing the X-ray machine, and it is preferably taken in a length of approximately 36 inches to provide a full size frontal view of the patient's spine 46. Accordingly, the X-ray can thereafter be utilized for determining the precise locations of the apex and ends of one or more curves that may exist in the patient's spine 46. Specifically, the X-ray is oriented in an aligned relation to the patient to determine the precise locations of the apex and ends of the curves in the spine 46 relative to the exterior of the torso portion of the patient 12. During this procedure the patient is preferably dressed in one or more long disposable cotton stockinets which provide a suitable tight garment to which markings can be applied in order to designate the locations of the apex and ends of the one or more curves in the patient's spine. The one or more cotton stockinet garments also provide suitable protection for the patient 12 during subsequent steps of the method in which the cast 14 is formed.

Once the precise locations of the apex and ends of a scoliotic curve and any additional curves, including any compensatory curves, have been determined relative to the exterior of the torso portion of the patient 12 in the above manner, the apparatus 10 is utilized to position the patient 12 in a treatment position both prior to and during the formation of the cast 14. Specifically, the patient 12 is first positioned on the casting board 18, and the pressure pads 20 and 22 are assembled on the casting board 18 to apply appropriate amounts of pressure to the torso portion of the patient 12. In this regard, the patient 12, as herein illustrated, includes a spine 46 having a single lateral curve therein, and therefore, a total of three pressure pads 20 and 22 are required to apply pressure to the apex and ends of the curve in the spine 46. However, it will be understood that patients having spines with more complex curves, including those having reverse or compensatory curves, normally require the use of at least one additional pad 20 or 22 for each additional curve. Further, it will be understood that it is also possible utilize the pads 20 or 22 interchangeably, although preferably at least one of the pads 20 or 22 is adjustable to enable appropriate amounts of pressure to be more easily applied to the patient 12. In this regard, the adjustable pressure pad 22 is preferably utilized for applying pressure to the apex of the scoliotic curve, whereas the nonadjustable pads 20 are preferably used to apply pressure to the opposite ends of the curve. In any event, as herein illustrated, the patient 12 is positioned on the board 24 in a laying-down, face-up position, and the pads 20 and 22 are assembled on the board 24 so that they are positioned on opposite sides of the torso portion of the patient 12. In this regard, the pads 20 and 22 are precisely positioned relative to the patient 12 so that they are operative for applying compensatory pressure to the apex and ends of the scoliotic curve in the spinal column 46. However, it will be appreciated that because the pads 20 and 22 can only apply indirect pressure to the spine 46 through the ribs or other adjacent components of the torso portion, they are not necessarily always positioned directly adjacent the ends and apex of the scoliotic curve. For example, as illustrated in FIG. 3, the upper pad 20 is positioned under the right arm of the patient 12 for applying pressure to the upper end of the scoliotic curve which is located at the base of the patient's neck. This because the upper pad 20 is operative for indirectly applying pressure to the spine 46 through the upper ribs of the patient 12 which angle upwardly and inwardly to the spine 46. In any event, it will be understood that compensations of this type can be readily preformed in accordance with conventional medical procedures by persons skilled in the related medical art. Once the patient 12 has been assembled on the apparatus 10 and the pressure pads 20 and 22 have been placed in engagement with the patient 12 so that they are in proper longitudinal positions relative to the spine 46, the pressure pad 22 is further adjusted to apply the appropriate amounts of lateral pressure to the sides of the torso portion of the patient 12. During this operation, the load cell 35 is utilized for monitoring the amount of pressure applied to the patient 12 with the pads 22, it being understood that those skilled in the related medical art are aware of the appropriate amounts of pressure which can be safely applied to the torso portion depending on the age, sex and overall size of the patient 12 and the positions of the pressure pads 20 and 22. In any event, once the pressure pads 20 and 22 have been adjusted to apply the proper amounts of pressure to the torso portion of the patient 12, the precise locations of the pressure pads 20 and 22 on the board 24 as well as the precise location of the patient 12 thereon are noted, and one or more of the pads 20 and/or 22 and the patient 12 are removed from the board 24.

In the next step of the method an uncured cast 14 is assembled on the torso portion of the patient 12 in a conventional manner, such as by wrapping the torso portion with uncured fast-setting plaster bandages so as to cover substantially the entire torso portion. Thereafter, a protective plastic layer 48 is wrapped around the uncured cast 14 to protect the apparatus 10. The patient 12 with the cast 14 and the protective wrap 47 thereon is then repositioned on the board 24 along with the pressure pads 20 and 22. In this regard, when repositioning the patient 12 and the pressure pads 20 and 22 on the board 24 it is important to be certain that the patient 12 is in substantially the same treatment position as when the pressure pads 20 and 22 were originally positioned to apply the appropriate amounts of pressure to the torso portion of the patient 12. Further, it is also important to be certain that the pressure pads 20 and 22 are repositioned in the same pressure applying positions on the board 24. In any event, once the patient 12, the uncured cast 14, the outer wrap 48 and the pressure pads 20 and 22 have been repositioned on the board 24, the cast 14 is allowed to cure while the patient 12 is held in a proper treatment position with the pressure pads 20 and 22. Accordingly, the cast 14 is retained in a position which enables it to thereafter be effectively utilized for fabricating a brace which is capable of applying precise predetermined amounts of pressure to prespecified areas of the spine 46 of the patient 12.

Once the cast 14 has been allowed to cure, the patient 12, the cast 14 and one or more of the pads 20 and/or 22 are removed from the board 24, and the cured cast 14 is removed from the patient 12 by conventional techniques. In this regard, however, care must be taken to prevent excessive damage to the cured cast 14 so that it can be effectively reassembled to provide a form or mold which can be utilized in the fabrication of a suitable brace for the patient 12. Accordingly, once the cast 14 has been removed from the patient 12, it is repaired by conventional techniques to provide a suitable tubular form for use in fabricating the brace 16.

Figure 7:
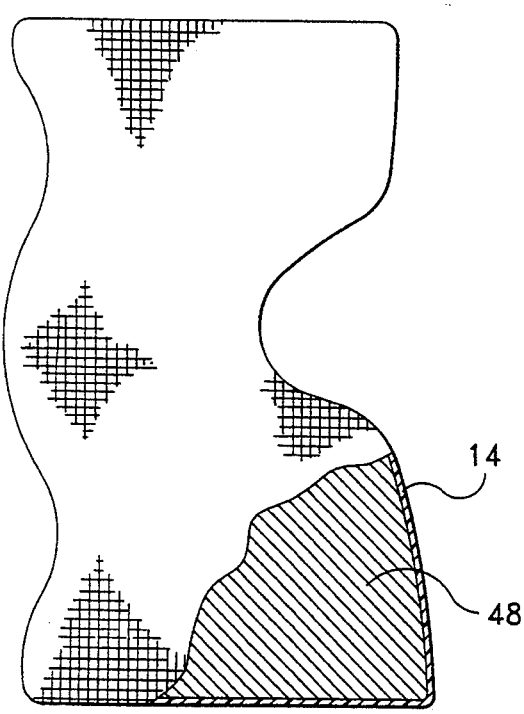
FIG. 7 is a front elevational view of the cast as used for forming a positive impression of the patient.
Figure 8:
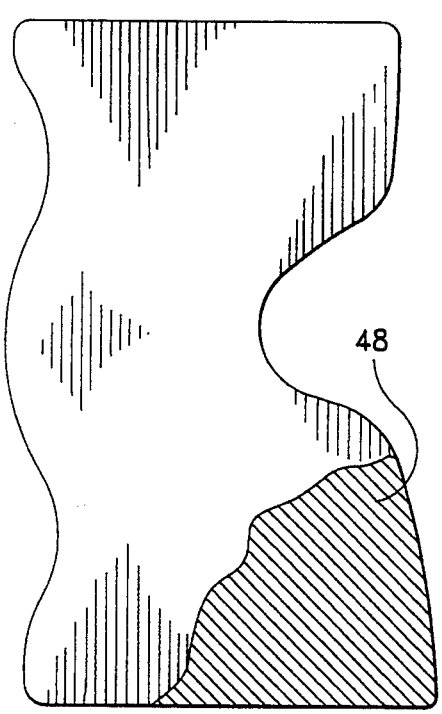
FIG. 8 is a front elevational view of a positive impression of the patient made with the cast.
Figure 9:
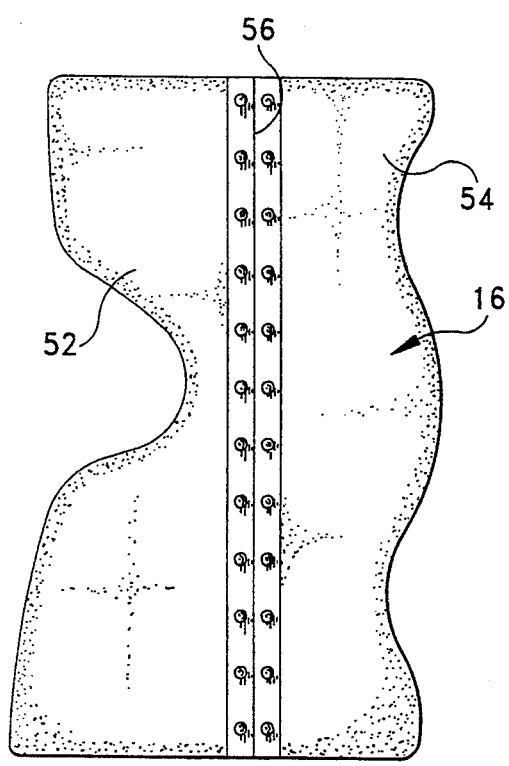
FIG. 9 is a front elevational view of a brace made from the positive impression illustrated in FIG. 7.
Figure 10:
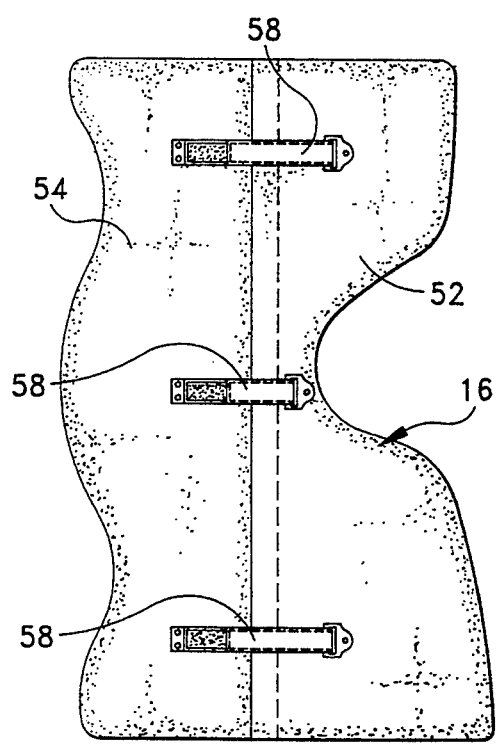
FIG. 10 is a rear elevational view of the brace.

Once the cured cast 14 has been removed from the patient 12 and any necessary repairs to the cast 14 have been completed, the cast 14 is utilized for forming a brace for the patient 12 in accordance with conventional techniques. More specifically, the lower end of the cast 14 is preferably closed and the cast 14 is preferably filled with a suitable conventional casting material, such as a plaster of paris based composition, to form a positive impression 48 of the patient as illustrated in FIGS. 7 and 8. The positive impression 48 is then finished by conventional techniques to provide a smooth finished form of the torso portion of the patient 12 as distorted to apply the appropriate predetermined amounts of corrective pressure to the spinal column 46 of the patient 12. Finally, a brace 16 is formed over the finished positive impression 48. The brace 16 preferably includes left and right halves 52 and 54, respectively which are preferably individually formed on the impression 48 from a polypropelene copolymer. The left and right halves 52 and 54 are hingably connected along a hinge line 56 in the back of the brace 16 which is preferably defined by a living hinge segment of polypropelene copolymar. Provided on the front side of the brace 16 is a plurality of strap assemblies 58 which are operative for releasably securing the left and right halves 52 and 54 together on the front side of the patient 12. The strap assemblies 58 preferably comprise conventional hook and pile type fastening assemblies, and they are permanently secured to the halves 52 and 54 as illustrated. Once the brace 16 has been fully formed in this manner, it is assembled on the patient 12 and any necessary final adjustments to the brace 16 are performed by conventional techniques.

It is seen therefore that the instant invention provides an effective method and apparatus for forming a brace 16 for a scoliosis patient. The apparatus 10 is effectively operable in accordance with the method for forming the brace 16 in a manner which enables the brace 16 to be utilizes for effectively accurately applying controlled amounts of pressure to the torso portion of the patient so as to correct one or more lateral curves in the spinal column 46. In this regard, by positioning the patient 12 on the casting board 24 and assembling the pressure pads 20 and 22 with the casting board 24 so as to apply controlled and well defined amounts of pressure to prespecified areas of the spinal column 46 and then repositioning the patient 12 and the pressure pads 20 and 22 on the casting board 24 after the uncured cast 14 has been assembled on the patient, it is possible to form the cast 14 in an appropriate configuration for accurately and effectively applying desired amounts pressure to the spinal column 46. Hence, by forming the brace 16 in a similar configuration, it is possible to form the brace 16 so that it is also effectively capable of accurately applying prespecified amounts of pressure to the spinal column 46. In fact, it has been found that the method and apparatus of the subject invention can be effectively utilized to achieve corrections in areas of curvature of the spinal columns of patients in the range of between 93% and 95%. Hence, it is seen that the method and apparatus of the instant invention represent extremely significant advancements in the medical art which have substantial commercial significance.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A method of forming a brace for a scoliosis patient, the patient including a torso portion and a spine having a lateral scoliotic curve, the scoliotic cure having an apex and having opposite ends, said method comprising:
    a. determining the location of the apex and ends of the scoliotic curve relative to the exterior of the torso portion of the patient;
    b. positioning the patient in a laying-down treatment position on a casting board;
    c. applying pressure to opposite sides of the torso portion of the patient utilizing at least three pressure pads, the pressure pads being positioned on the casting board in pressure applying positions in which the pressure pads are operative for applying desired amounts of pressure to the spine at substantially the ends and apex of the scoliotic curve in directions tending to straighten the scoliotic curve;
    d. removing the patient from the casting board;
    e. applying an uncured cast to the torso portion of the patient;
    f. repositioning the patient in the treatment position on the casting board with the at least three pressure pads in the pressure applying positions thereof on the casting board;
    g. allowing the uncured cast to cure;
    h. removing the patient from the casting board;
    i. removing the cast from said patient; and
    j. forming the brace so that it has an internal configuration which corresponds substantially to that of the cast.

2. In the method of claim 1, at least one of the pressure pads including pressure sensing means, said step of applying pressure including determining the amount of pressure applied to the patient with the at least one pressure pad utilizing the pressure sensing means thereof to apply a desired amount of pressure to the spine.

3. In the method of claim 1, said step of applying pressure further comprising applying pressure to the apex of the scoliotic curve utilizing an adjustable pressure pad which is adjustable for applying variable amounts of pressure to the spine.

4. In the method of claim 2, said step of applying pressure further comprising applying pressure to the apex of the scoliotic curve utilizing an adjustable pressure pad which is adjustable for applying variable amounts of pressure to the spine.

5. In the method of claim 1, said step of determining the locations of the apex and ends of the scoliotic curve including taking an X-ray of the spine positioning the X-ray in substantially aligned relation to the patient and applying markings to the patient corresponding to the locations of the apex and ends of the scoliotic curve.

6. In the method of claim 1, pressure pads bring releasably securable at a plurality of predetermined positions on the casting board, said step of applying pressure comprising applying pressure utilizing at least three pressure pads, each of the pressure pads being positioned at one of the predetermined positions on the casting board which corresponds to the respective pressure applying position thereof, said step of repositioning the patient in the treatment position including repositioning the at least three pressure pads in the predetermined positions on the casting board which correspond to the respective pressure applying positions thereof.

7. In the method of claim 1, said step of forming the brace so that the brace has an internal configuration which corresponds substantially to the cast including forming a positive impression of the torso portion in the cast and forming the brace from the positive impression.

8. The method of claim 7 further comprising assembling a pressure sensing device in the brace at a location therein corresponding to the position of the pressure applied by one of the pressure pads to the patient.

9. A method of forming a cast for a brace for a scoliosis patient, the patient including a torso portion and a spine having a lateral scoliotic curve, the scoliotic curve having an apex and having opposite ends, said method comprising:
   a. determining the locations of the apex and ends of the scoliotic curve relative to the exterior of the torso portion of the patient;
   b. positioning the patient in a laying-down treatment position on a casting board;
   c. applying pressure to opposite sides of the torso portion of the patient utilizing at least three pressure pads, the pressure pads being positioned on the casting board in pressure applying positions in which the pressure pads are operative for applying desired amounts of pressure to the spine at substantially the ends and apex of the scoliotic curve in directions tending to straighten the scoliotic curve;
   d. removing the patient from the casting board;
   e. applying an uncured cast to the torso portion of the patient;
   f. repositioning the patient in the treatment position on the casting board with the at least three pressure pads in the pressure applying positions thereof on the casting board;
   g. allowing the uncured cast to cure;
   h. removing the patient from the casting board; and
   i. removing the cast from the patient.

10. In the method of claim 9, at least one of the pressure pads including pressure sensing means, said step of applying pressure including determining the amount of pressure applied to the patient with the at least one pressure pad utilizing the pressure sensing means thereof to apply a desired amount of pressure to the spine.

11. In the method of claim 9, said step of applying pressure further comprising applying pressure to the apex of the scoliotic curve utilizing an adjustable pressure pad which is adjustable for applying variable amounts of pressure to the spine.

12. In the method of claim 10, said step of applying pressure further comprising applying pressure to the apex of the scoliotic curve utilizing an adjustable pressure pad which is adjustable for applying variable amounts of pressure to the spine.

13. In the method of claim 9, said step of determining the locations of the apex and ends of the scoliotic curve including taking an X-ray of the spine, positioning the X-ray in substantially aligned relation to the patient and applying markings to the patient corresponding to the locations of the apex and ends of the scoliotic curve.

14. In the method of claim 9, the pressure pads bring releasably securable at a plurality of predetermined positions on the casting boards, said step of applying pressure comprising applying pressure utilizing at least three pressure pads, each of the pressure pads being positioned at one of the predetermined positions on the casting board which corresponds to the respective pressure applying position thereof, said step of repositioning the patient in the treatment position including repositioning the at least three pressure pads in the predetermined positions on the casting board which correspond to the respective pressure applying positions thereof.

15. In the method of claim 9, said step of forming the brace so that the brace has an internal configuration which corresponds substantially to the cast including forming a positive impression of the torso portion in the cast and forming the brace from the positive impression.

16. The method of claim 15 further comprising assembling a pressure sensing device in the brace at a location therein corresponding to the position of the pressure applied by one of the pressure pads to the patient.

* * * * *